United States Patent [19]
Santilli et al.

[11] Patent Number: 5,967,972
[45] Date of Patent: Oct. 19, 1999

[54] MINIMALLY INVASIVE SURGICAL RETRACTOR AND METHOD OF OPERATION

[75] Inventors: Albert N. Santilli, Pepper Pike, Ohio; Alex Zapolanski, San Mateo, Calif.; Amit Patel, Cleveland Heights, Ohio

[73] Assignee: Kapp Surgical Instrument, Inc., Cleveland, Ohio

[21] Appl. No.: 09/049,597

[22] Filed: Mar. 27, 1998

Related U.S. Application Data

[60] Provisional application No. 60/042,472, Mar. 28, 1997.

[51] Int. Cl.$^6$ ...................................................... A61B 17/00
[52] U.S. Cl. ........................... 600/232; 600/201; 600/206; 600/229; 600/235
[58] Field of Search ...................................... 600/201, 205, 600/206, 210, 229, 228, 227, 231, 232, 235

[56] References Cited

U.S. PATENT DOCUMENTS

| Re. 34,150 | 12/1992 | Santilli et al. . |
|---|---|---|
| 1,311,313 | 7/1919 | Brix . |
| 4,424,724 | 1/1984 | Bookwalter et al. . |
| 4,747,395 | 5/1988 | Brief .................................. 600/210 |
| 5,865,730 | 2/1999 | Fox et al. ............................ 600/229 X |
| 5,875,782 | 3/1999 | Ferrari et al. ....................... 600/235 X |
| 5,876,332 | 3/1999 | Looney ................................ 600/227 |

FOREIGN PATENT DOCUMENTS

| 1360707 | 12/1987 | U.S.S.R. ............................... 600/227 |
|---|---|---|

OTHER PUBLICATIONS

Jakoscope Brochure, Atlantis Surgical, 1996, Milltown, New Jersey.

Ron Winslow, Hope and Hype Follow Heart–Surgery Method That's Easy on Patients, Wall Street Journal, Apr. 22, 1997.

"Beating Heart Bypass—A New Approach", Cardio Thoracic Systems (brochure), Cupertino CA, 1996.

"Mini–CABG Access Set", United States Surgical Corporation, Norwalk CT, Cardiovascular Marketing Newsletter, vol. I, No. 1, Nov. 1996.

*Primary Examiner*—Jeffrey A. Smith
*Attorney, Agent, or Firm*—Rankin, Hill, Porter & Clark LLP

[57] ABSTRACT

A retractor for use in various types of surgical procedures such as harvesting mammary arteries, coronary bypass surgery, heart valve repairs, mitral valve replacement, partial sternotomies, and other types of surgery includes a toothed crossbar to which a pair of small grips are attached. The first grip is attached to an arm which is removably connected to a first block. The first block is movable along the crossbar, thereby permitting the first grip to be moved toward or away from the second grip. The second grip is attached to an arm which is removably connected to a second block. The second block can be fixed or movably connected to the crossbar. The crossbar includes a hinge that enables the grips to be pivoted relative to each other. Pivoting is accomplished by a pair of vertically extending brackets that are connected to the blocks and which are connected to each other by an adjustable connector. Retractor blades of various types are connected to the adjustable connector or to arm-carried rods by universal clamps. The grips can be removed and replaced with differently configured grips in order to conduct different types of surgical procedures or to conduct surgical procedures on different portions of a patient's body. The retractor according to the invention enables one portion of a patient's body to be both retracted and raised relative to an adjacent portion of the body. Such retraction provides effective access to a surgical site with minimal invasion of the body.

39 Claims, 14 Drawing Sheets

MINIMALLY INVASIVE SURGICAL RETRACTOR AND METHOD OF OPERATION

REFERENCE TO PROVISIONAL APPLICATION

Reference is made to provisional application serial no. 60/042,472, filed Mar. 28, 1997, the disclosure of which is incorporated herein by reference and from which priority is claimed.

BACKGROUND OF THE INVENTION

1. Field of the Invention

The invention relates to retractors that are used in various types of surgeries such as cardiovascular surgery and, more particularly, to a retractor that permits such operations to be conducted with minimal trauma to the patient.

2. Description of the Prior Art

In the course of such operative procedures as mitral valve surgery, it is necessary to expose the heart. Such exposure traditionally has been accomplished by performing a sternotomy (cutting an incision completely through the sternum and retracting the sternum). The retraction is accomplished by a retractor that employs parallel grips that engage the edges of the separated sternum. The grips are mounted perpendicularly to a toothed crossbar. One of the grips is fixed to one end of the crossbar, while the other grip is movably mounted to the crossbar by means of a pinion that engages the teeth of the crossbar. Upon rotating the pinion, the movable grip can be moved away from the fixed grip, thereby retracting the sternum so as to expose the heart. A retractor of the type described is shown in U.S. Pat. No. Re. 34,150, issued Dec. 29, 1992 to A. E. Santilli and D. M. Cosgrove III ("the '150 patent"), the disclosure of which is incorporated herein by reference.

After the sternum has been retracted, it is necessary to retract portions of the heart in order to expose diseased or defective parts thereof. Such retraction has been accomplished by attaching a cardiovascular retractor to one of the grips of the sternum retractor. The cardiovascular retractor, in preferred form, includes a horizontal rod to which retractor blades having elongate handles are attached by means of universal clamps. The rod is spaced above the grip a considerable distance in order to permit the blades to have access to the heart at a favorable angle. The blades can be moved so as to engage portions of the heart to be retracted. Thereafter, upon pulling the blades and locking them in place by tightening the universal clamps, the heart can be retracted in any manner desired and maintained in that position as long as necessary.

The blades in the described construction can be moved back and forth, up and down, side to side, and they can be pivoted about the longitudinal axis of the handle. Such versatility enables the device to be used for virtually any type of heart operation where retraction is required. A preferred example of the device in question is disclosed in the '150 patent.

While the retractor disclosed in the '150 patent is effective for retraction of the sternum and subsequent retraction of the heart, unfortunately the operative technique is very invasive. That is, the splitting of the sternum coupled with its retraction is an extremely traumatic procedure. The recovery time from such a procedure can be significant. Further, the patient will experience considerable pain and discomfort during the recovery process. It is possible that the trauma associated with the process can have a negative impact on the patient's recovery from the operation.

Desirably, a retractor would exist that would permit surgical procedures to be performed that are less invasive than are possible with presently available retractors. Preferably, any such retractor would be relatively small and lightweight compared with prior retractors.

SUMMARY OF THE INVENTION

In accordance with the present invention, a new and improved retractor is disclosed that is minimally invasive. The invention also includes a new and improved method of retraction. By using the present invention, the heart can be accessed through a small incision between the ribs on the left side of the chest, usually between the third and fourth ribs. The right side of the chest also can opened in this manner for various purposes such as harvesting the right-side mammary artery. If it is desired to approach the heart through the sternum, only a small opening in the sternum is required. Further, the present invention permits certain heart operations to be performed without the need to stop the heart and use a heart-lung machine. In addition to heart surgeries, the present invention also enables other types of operations to be performed more effectively that has been possible heretofore.

The retractor according to the invention is provided in two embodiments for use in different surgical procedures as the surgeon may determine. In one embodiment, the retractor includes a pair of small grips, or paddles, that are mounted to an elongate crossbar. The grips are disposed at the ends of arms that are connected removably to blocks that are connected to the crossbar. One of the blocks is fixed to one end of the crossbar, while the other block is movable along the crossbar so as to move toward or away from the fixed grip. The movable block is moved along the crossbar by means of a pinion that engages teeth on the crossbar. The pinion has a handle (or wrench) in order to permit the block to be moved readily.

The crossbar in the present invention includes a hinge disposed at a location between its ends and between the spaced grips. The hinge is movable about an axis that is perpendicular to the longitudinal axis of the toothed portion of the crossbar and parallel to, or coincident with, a plane in which the toothed portion of the crossbar lies. Accordingly, the hinge enables one end of the crossbar to be pivoted which, in turn, enables the fixed grip to be pivoted relative to the movable grip. Preferably, the hinge enables the fixed grip to be moved through an angle of +45 degrees and −45 degrees relative to the longitudinal axis of the toothed portion of the crossbar.

The invention includes means for pivoting the fixed grip about the axis of the hinge. The means for pivoting can take two forms. In the first form, a first, vertically extending bracket is secured removably to one of the blocks and a second, vertically extending bracket is secured removably to the other block. An elongate rod having first and second opposed ends is pivotally connected at its first end to the first bracket and adjustably connected at its second end to the second bracket. Preferably, the second bracket includes an opening through which the second end of the rod extends. The second end of the rod is threaded and carries a nut for engaging the second bracket.

When the crossbar is positioned in a straight line, i.e., not pivoted, the rod is parallel to the longitudinal axis of the crossbar. The rod is connected to the brackets such that it is disposed above the crossbar a desired amount. When the nut is tightened and/or when the grips are moved apart, the fixed grip will be pivoted relative to the movable grip.

The invention also includes so-called side arm attachments. These attachments are elongate rods that can be removably attached to either of the arms. The rods enable one or more retractor blades of conventional design having elongate handles to be used to retract portions of the heart. Each retractor blade is connected to a selected rod by means of a universal clamp that encircles the handle of the blade and which is attached to the rod. Each clamp includes a nut that enables the clamp to be tightened or loosened with one hand. The clamps permit the blades to be moved to any position that may be desired by the surgeon.

The invention is especially effective for certain types of heart surgeries when employing a retractor blade known as a stabilizer. The stabilizer in question has an elongate handle to which a pair of spaced, parallel, generally flat fingers are connected at one end. The fingers lie in a plane disposed at an angle of approximately 125 degrees from the longitudinal axis of the handle. The stabilizer enables the heart to be compressed so as to be rendered relatively motionless. The region of the heart between the spaced-apart fingers will be relatively starved for blood, thereby permitting surgery to be performed without the need for a heart-lung machine to stop the heart. In order to accommodate different operative conditions, the stabilizer can be provided with malleable fingers, a malleable neck, or with an adjustable ball and socket connection between the handle and the fingers.

A particularly effective technique for supporting the stabilizer is to provide a housing that can be connected to a selected block. The stabilizer is connected to the housing by a flexible member that can be secured in a rigid position when desired. Preferably, the flexible member includes a plurality of generally tubular members disposed in end-to-end relationship, a cam disposed within the housing, a fitting (to which the stabilizer is connected) disposed at the end of the generally tubular members, and a cable extending through the generally tubular members. Upon activating the cam, the cable will be tightened or loosened, thereby securing the stabilizer in place or permitting it to be moved. An adjustment mechanism also can be provided for pre-tensioning the generally tubular members.

In a second embodiment of the invention, both blocks are movably mounted on the crossbar. This permits each arm with its respective grip to be positioned at any desired location relative to the hinge.

The invention also includes a second form of the means for pivoting the crossbar. The second form includes first and second brackets that are connected to the first and second blocks, respectively. The brackets are connected by a toothed rod, or rack, that is affixed to one of the brackets and which extends through an opening in the other bracket. The other bracket includes a pinion that can be rotated by a wingnut. A spring-biased pawl prevents the brackets from moving away from each other while permitting the brackets to move toward each other, thereby causing the crossbar to be pivoted.

The method according to the invention comprises a particular technique for retracting the patient's ribs or sternum most effectively. The method in question involves compressing the distal ribs, while retracting and raising the adjacent proximal ribs. This result is accomplished by orienting the crossbar such that the movable grip is on the distal side of the patient.

Initially, the hinge is positioned to provide a straight crossbar and the grips are moved together in order to insert them between the ribs. The means for pivoting is actuated in order to pivot the fixed, or proximal, grip about the axis of the hinge. Then, the grips are moved apart by moving the distal grip along the crossbar. As the distal grip is moved, the grips are spaced further apart and the proximal grip is raised even further. Such retraction provides adequate access to the heart despite the small incision between the ribs.

The retractor according to the invention can be used for operations on either side of the chest. By orienting the crossbar appropriately, the retractor can always be positioned to compress the distal ribs and retract and raise the proximal ribs. A similar result can be obtained with incisions through the sternum, that is, appropriate positioning of the blocks and brackets will enable either side of the sternum to be retracted and raised as may be desired.

As will be appreciated from the foregoing description, the retractor according to the invention is minimally invasive. By using the retractor according to the invention, adequate access to the heart can be obtained merely by making a small incision between two adjacent ribs. There is no need to completely split the patient's sternum in order to have access to the heart. The foregoing results are obtained by using very small grips and using the retractor first as a rib-spreader (or sternum spreader) and then as a proximal rib-lifter (or sternum lifter). Once the ribs or sternum have been retracted and raised properly, various attachments can be connected to the retractor for purposes of cardiovascular retraction and other purposes.

The retractor according to the invention also can be used for other types of surgeries, such as spinal implant surgery. The retractor can be used for both anterior and posterior spinal implant surgery. The ability to pivot and displace the fixed grip relative to the movable grip is a significant advantage compared with existing retractors. Further, because the grip-carrying arms are removably connected to the retractor, it is possible to substitute differently configured grips to conduct different types of surgical procedures, to conduct surgical procedures on different sizes of people, or to perform different types of retractions during the course of the same surgical procedure. Such substitutions can be accomplished quickly and easily, thereby enhancing the versatility of the retractor.

The foregoing features and advantages will be apparent from the accompanying drawings and the description that follows.

DESCRIPTION OF THE PREFERRED EMBODIMENT

Figure 1:
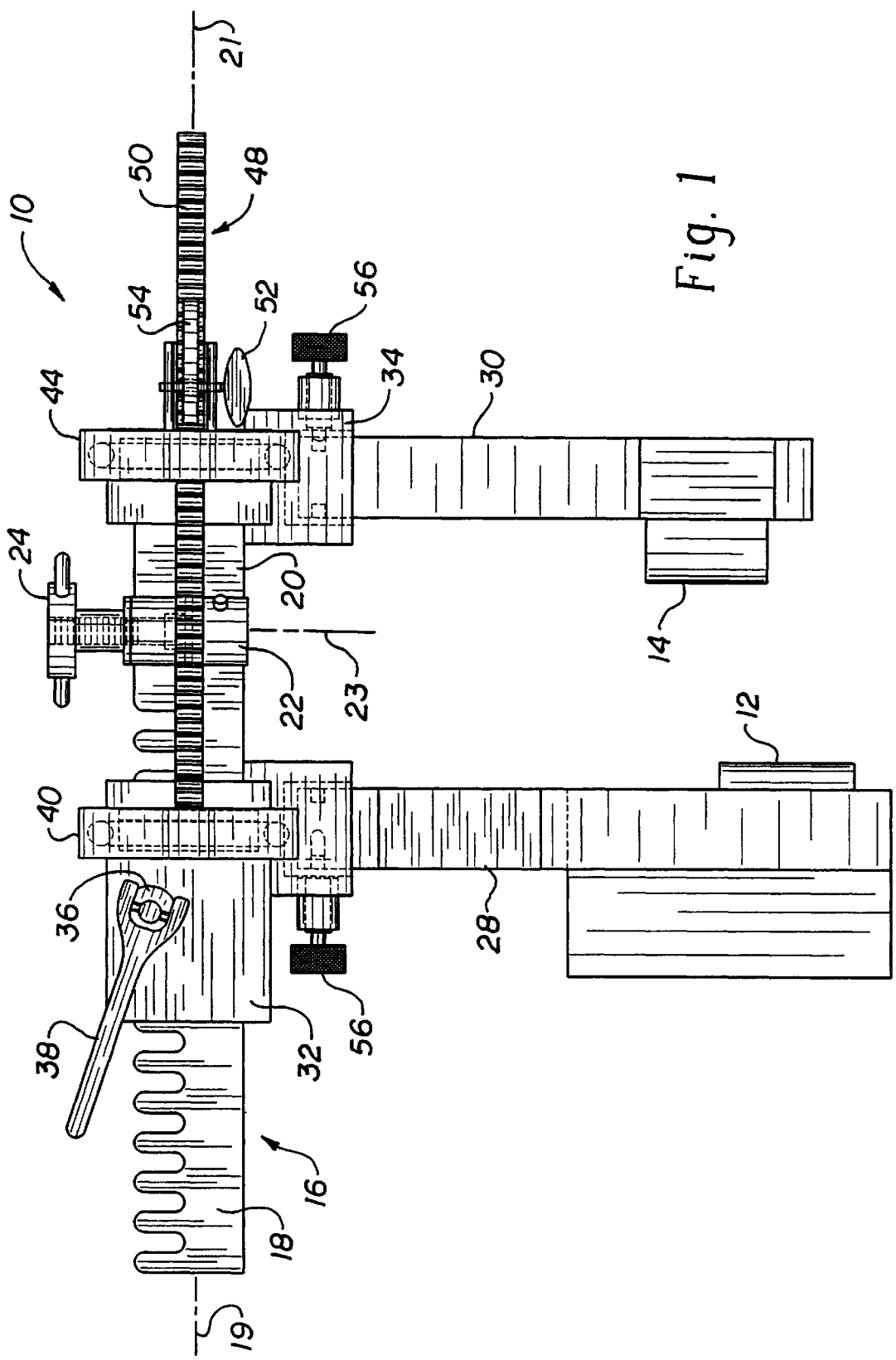
FIG. 1 is a top plan view of an assembled retractor according to the invention showing a movable block, a fixed block, and a toothed-rod pivoting device.
Figure 2:
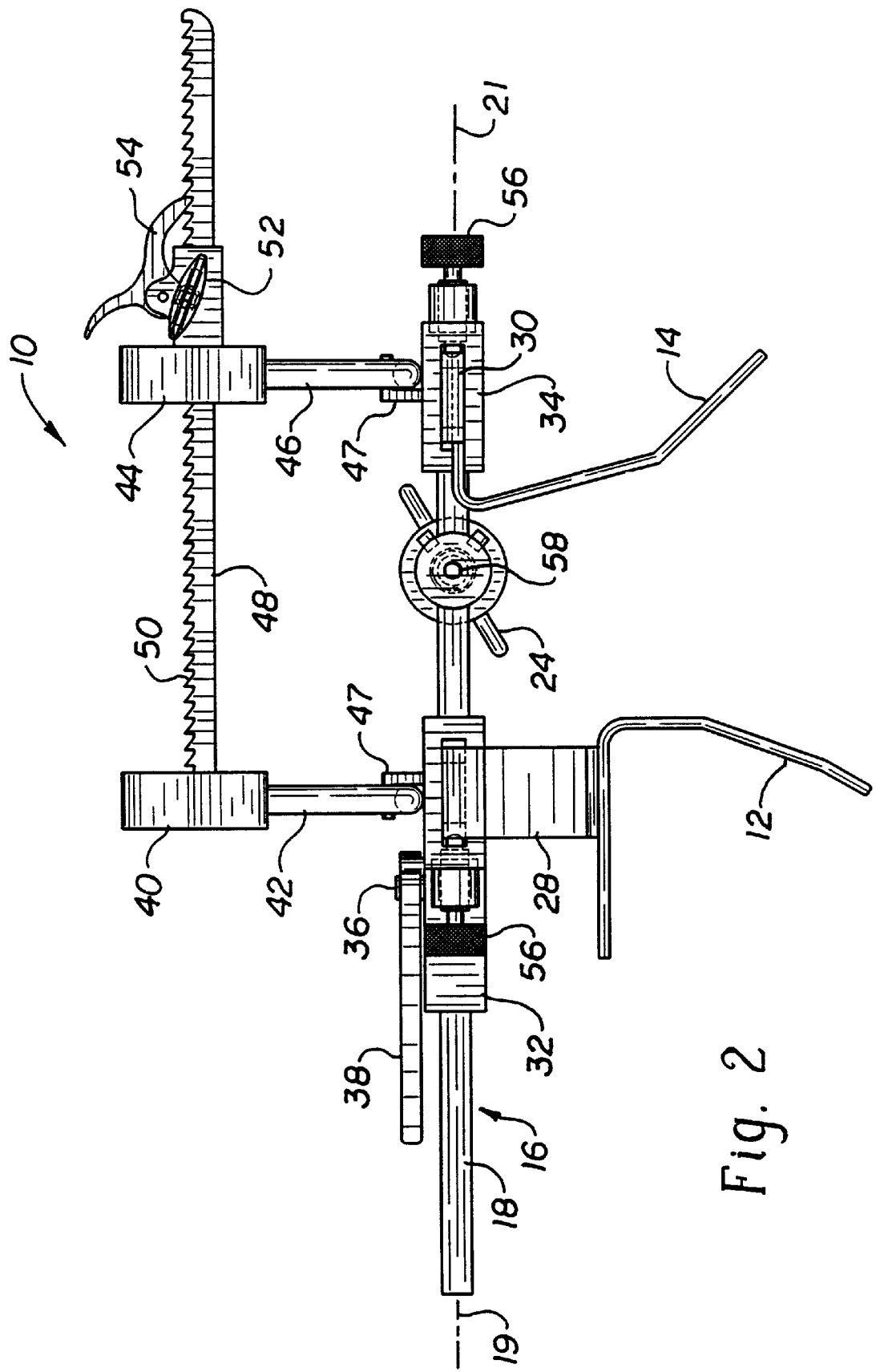
FIG. 2 is a front elevational view of the retractor of FIG. 1.
Figure 3:
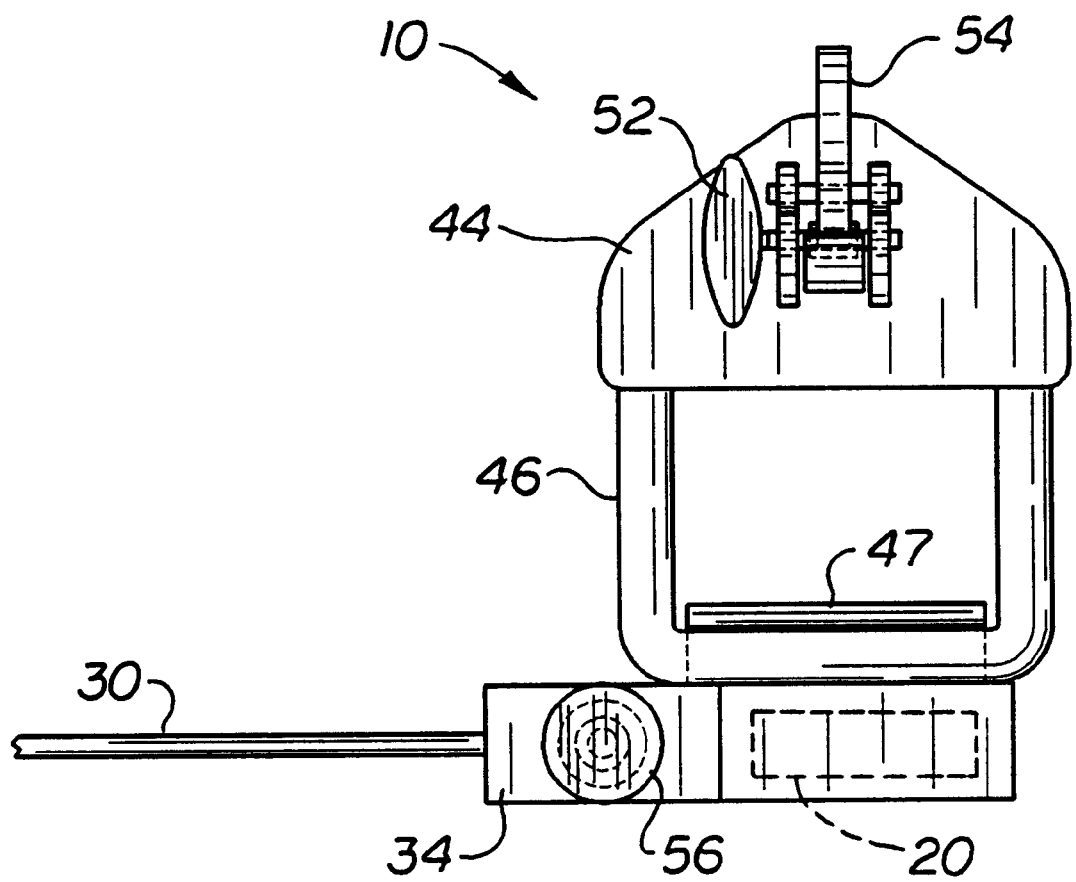
FIG. 3 is a side elevational view of the retractor of FIG. 1.
Figure 4:
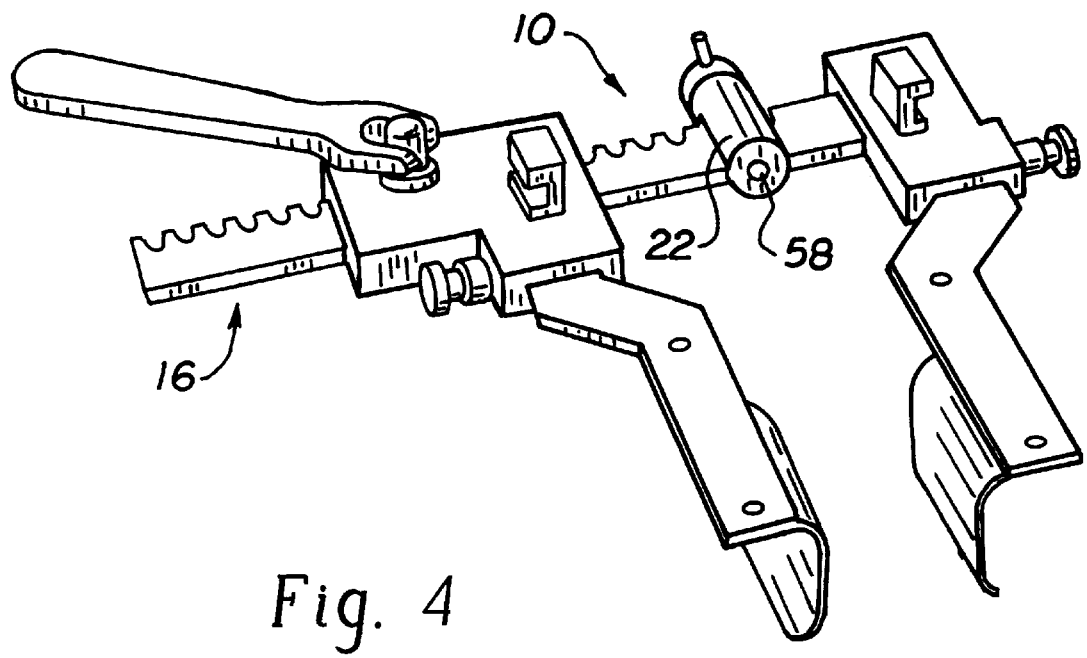
FIG. 4 is a perspective view of the retractor of FIG. 1 without a pivoting device and with different grips.

Referring particularly to FIGS. 1–3, a retractor according to the invention is indicated by the reference numeral 10. In the description that follows, reference should be made to the various other Figures, where appropriate, for a more detailed understanding of the individual components that are used with the invention.

The retractor 10 includes a pair of small, parallel grips 12, 14, or paddles, that are mounted to an elongate crossbar 16. The crossbar 16 includes a toothed portion 18 having a longitudinal axis 19 and a non-toothed portion 20 having a longitudinal axis 21. The crossbar 16 includes a locking, adjustable hinge 22 that connects the portions 18, 20 at a location between the spaced grips 12, 14. The hinge 22 pivots about an axis 23 that is perpendicular to the longitudinal axis 19 of the portion 18 and parallel to, or coincident with, a plane in which the axis 19 lies.

The hinge 22 enables the portion 20 to be pivoted relative to the portion 18 which, in turn, enables the grip 14 to be pivoted relative to the grip 12. Preferably, the hinge 22 enables the grip 12 to be moved through an angle of +45 degrees and −45 degrees relative to the longitudinal axis 19. The hinge 22 includes a lock 24 that can be tightened to prevent movement of the hinge 22 when a desired position of the grips 12, 14 has been attained.

The grips 12, 14 are disposed at the ends of arms 28, 30 that extend away from the crossbar 16. The arms 28, 30 are connected removably to blocks 32, 34, respectively, that are connected to the portions 18, 20. The block 34 is fixed to the portion 20, while the block 32 is movable along the portion 18 so as to move the grip 12 toward or away from the grip 14. Movement of the block 32 is accomplished by a pinion 36 that engages the teeth of the portion 18. A handle 38 is provided to rotate the pinion 36.

The invention includes a pivoting device for pivoting the grip 14 about the axis 28 of the hinge 26. The pivoting device in the preferred embodiment includes a first, vertically extending bracket 40 having a U-shaped ³⁄₁₆ inch steel rod 42. A second, vertically extending bracket 44 also has a U-shaped ³⁄₁₆ inch steel rod 46. The term "vertically" is used herein for purposes of convenience of description only. It is to be understood that the retractor 10 can be oriented in different positions, and the use of such terms of orientation as "vertically" is not to be construed as a limitation on the possible uses or orientations of the retractor 10.

The upper surfaces of the blocks 32, 34 each include an upside-down L-shaped bar 47. The bars 47 are welded or otherwise secured to the upper surfaces of the blocks 32, 34. The bars 47 are aligned along axes parallel to the axis 23 of the hinge 22, i.e., perpendicular to the longitudinal axes 19, 21. The undercut portions of the bars 47 face away from each other. The undercut portions are large enough to receive the rods 42, 46.

An elongate rod 48 is securely connected at one end to the first bracket 40. The second bracket 44 includes an opening through which the other end of the rod 48 extends. The upper surface of the rod 48 has a plurality of teeth 50. The bracket 44 includes a pinion that is operated by a wingnut 52. The pinion engages the teeth 50. A spring-biased pawl 54 also engages the teeth 50. As will be apparent from an examination of FIG. 2, the pawl 54 permits the brackets 40, 44 to be moved toward each other without interference, but prevents the brackets 40, 44 from being moved away from each other (unless released). When the lock 24 is loosened, the wingnut 52 can be rotated to cause the brackets 40, 44 to come closer together, thereby causing the grip 14 to be pivoted relative to the grip 12.

The blocks 32, 34 include slots adapted to receive the arms 28, 30. The arms 28, 30 are retained in the slots by notches (FIG. 9) that are engaged by spring-biased pins 56 included as part of the blocks 32, 34. Upon retracting the pins 56, the arms 28, 30 can be removed. Accordingly, the grips 12, 14 can be replaced quickly and conveniently by grips suited for other purposes. Grips of different configurations for different surgical procedures are shown in FIGS. 4–9. Some of the distal grips (FIGS. 5 and 9) includes malleable upper portions with rectangular openings that can be moved to different positions as the surgeon deems necessary.

The retractor 10 includes an external lock for the crossbar 16. Referring to FIGS. 4 and 6–8, the lock includes a plurality of prongs that are fitted over the crossbar 16 on either side of the hinge 22. The prongs extend from a base plate having an opening therein. A threaded pin extends through the opening and into an opening 58 included as part of the hinge 22 in order to securely attach the lock to the crossbar 16.

A rod (FIGS. 7 and 10) can be attached to either of the arms 28, 30. The rod preferably is L-shaped, although other configurations are possible. The rod includes a pair of small pins that project from one side thereof. The arms 28, 30 each include a pair of spaced openings in the upper surfaces thereof (FIGS. 4–9). The pins can be fitted into the openings to attach the rod to one of the arms 28, 30.

Figure 7:
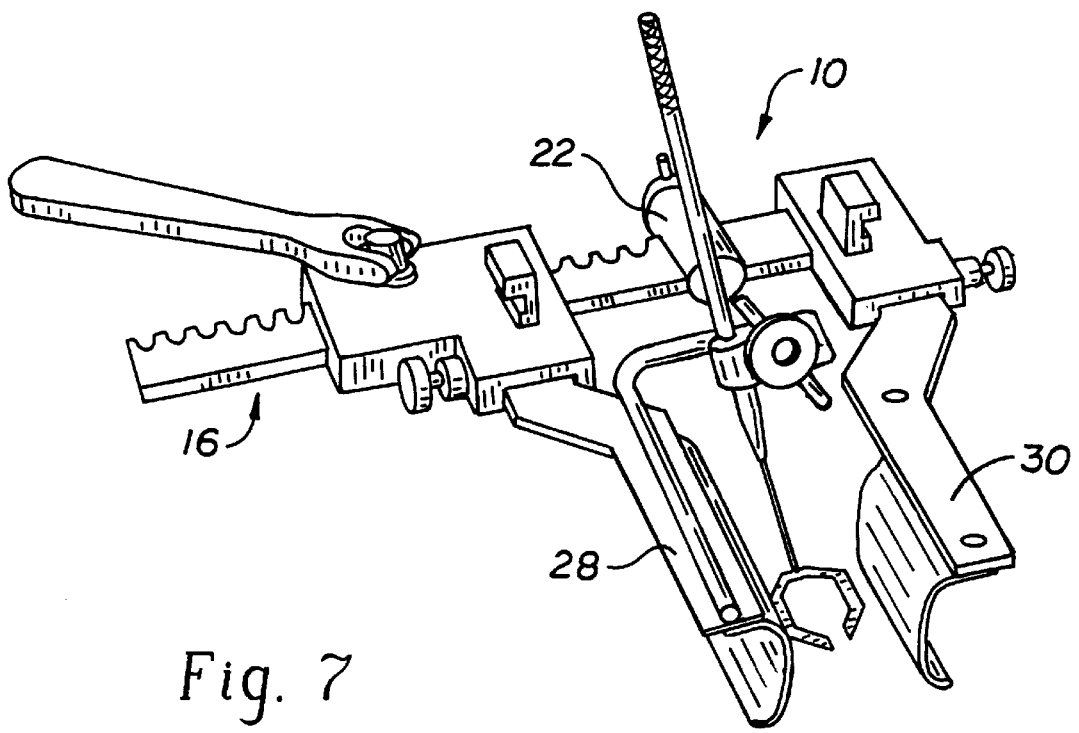
FIG. 7 is a perspective view of the retractor of FIG. 1 without a pivoting device and with a stabilizer held in place by a clamp that is connected to an arm-mounted rod.
Figure 8:
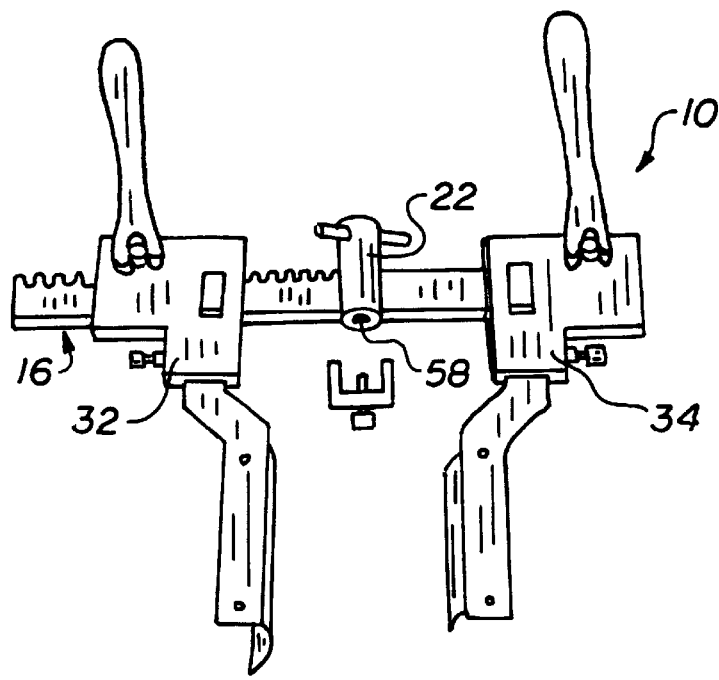
FIG. 8 is a photograph of the retractor according to the invention showing two grips being supported by movable blocks and a lock for connecting portions of a crossbar.

The rod enables one or more retractor blades of conventional design having elongate handles to be used to retract portions of the heart. Each retractor blade is connected to the rod by means of a universal clamp that encircles both the handle of the blade and the rod (FIG. 7). Each clamp includes a nut that enables the clamp to be tightened or loosened with one hand. The clamps permit the blades to be moved to any position that may be desired by the surgeon and quickly and easily locked in place there. Force applied to the rod by the retractor blade and the clamp biases the pins in the openings, thereby preventing the rod from being dislodged.

Figure 19:
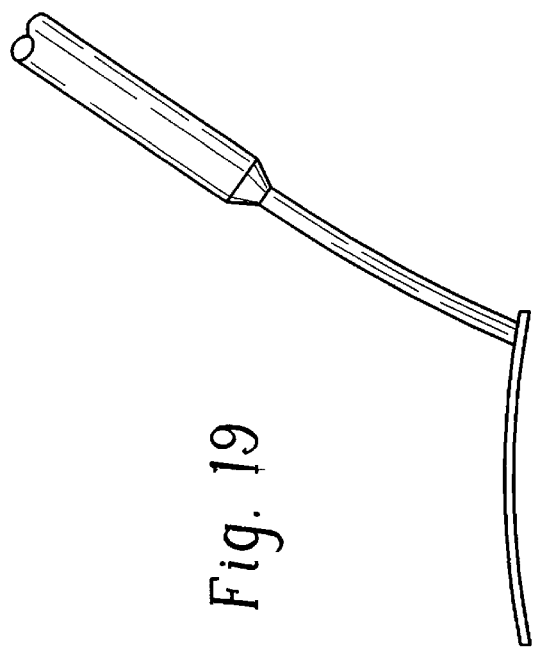
Figure 20:
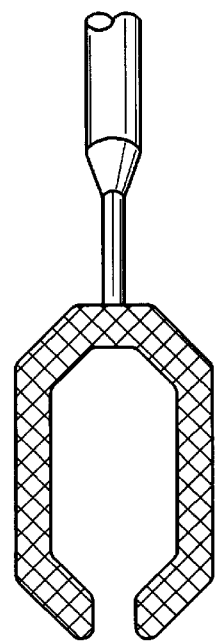

The invention is effective with a particular type of retractor blade known as a stabilizer. Referring to FIGS. 7 and 19–20, one form of the stabilizer has an elongate handle to which a pair of spaced, parallel, generally flat fingers are connected at one end. The fingers lie in a plane disposed at an angle of approximately 125 degrees from the longitudinal axis of the handle (see FIG. 19). The fingers are connected to the handle by a malleable neck, thus permitting the angular relationship between the fingers and the handle to be changed as the surgeon may see fit. If desired, the fingers also can be made of a malleable material for purposes of adjustment. The underside of the fingers are serrated. The retractor blade enables the heart to be compressed. The region of the heart between the spaced apart fingers will be relatively starved for blood, thereby permitting surgery to be performed without the need for a heart-lung machine to stop the heart.

Figure 21:
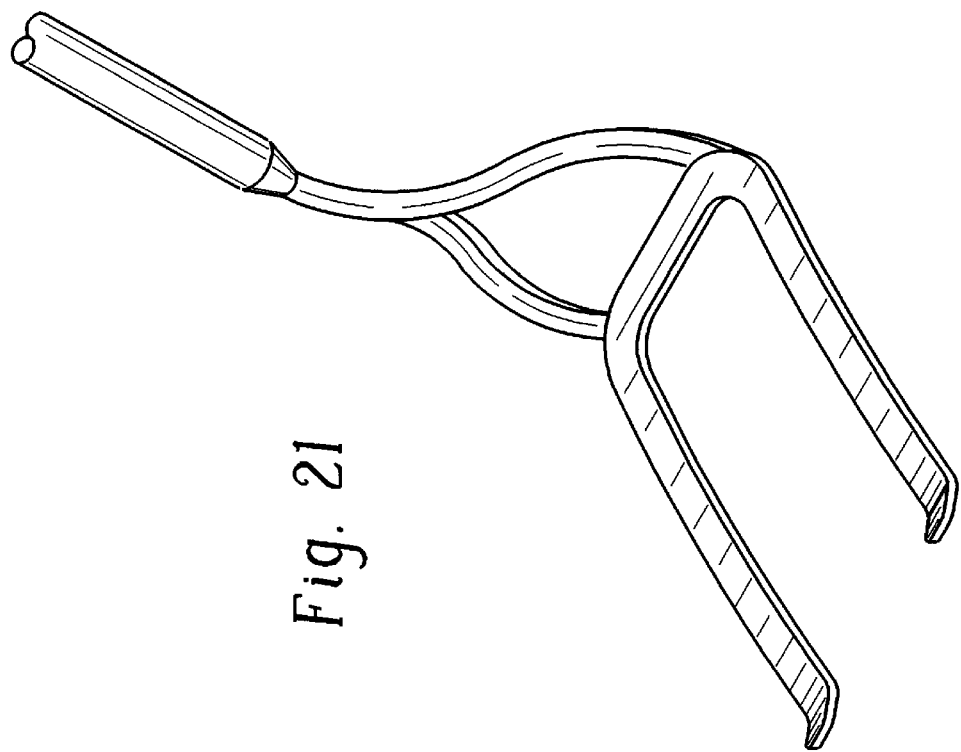
FIGS. 21, 22, and 23 are perspective, side, and bottom views, respectively, of another embodiment of a stabilizer according to the invention having a rigid neck.
Figure 22:
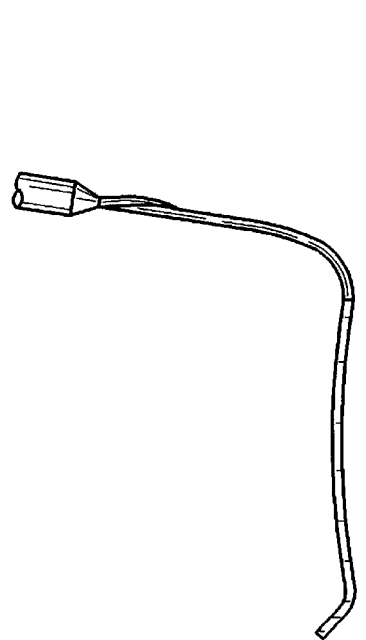
Figure 23:
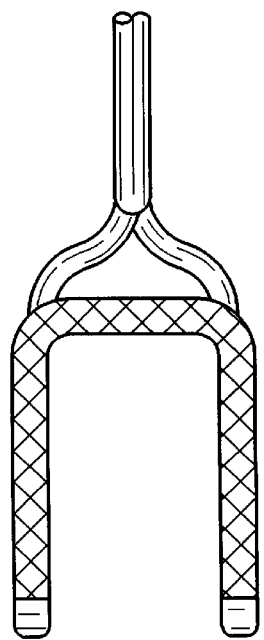
Figure 24:
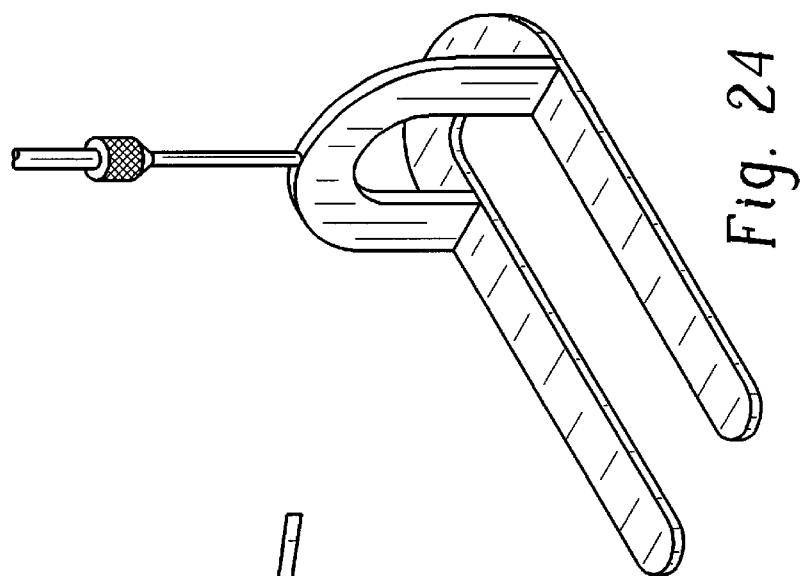
FIGS. 24, 25, 26, and 27 are perspective, side, and cross-sectional views, respectively, of another embodiment of a stabilizer according to the invention having a ball-and-socket adjustable neck.
Figure 25:
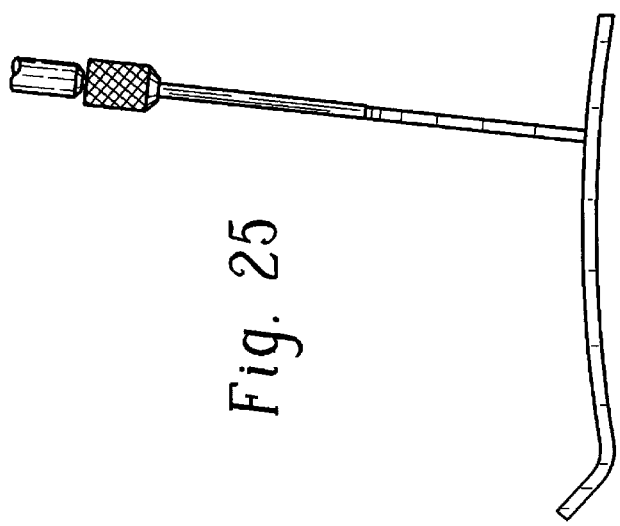
Figure 27:
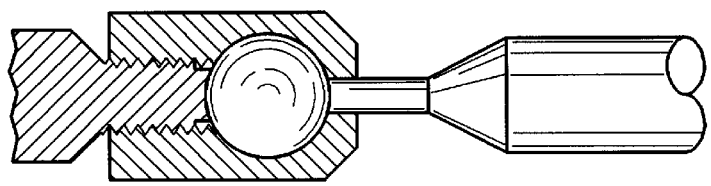
Figure 26:
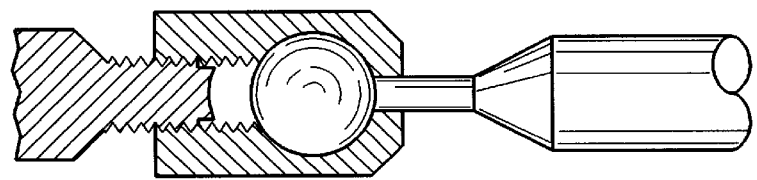

Another form of the stabilizer is shown in FIGS. 21–23. The stabilizer shown in FIGS. 21–23 is similar to the stabilizer shown in FIGS. 7 and 18–20, except that the neck is not malleable. The neck includes two portions that provide extra support for the fingers.

Yet another form of the stabilizer is shown in FIGS. 24–27. In this version of the stabilizer, the neck includes a ball that is fitted into a socket included as part of a threaded sleeve. The sleeve is threaded onto the end of the handle in order to compress the ball within the socket. By tightening or loosening the sleeve, the ball will be compressed or released. In turn, the position of the fingers relative to the handle can be adjusted as the surgeon may deem necessary.

Figure 10:
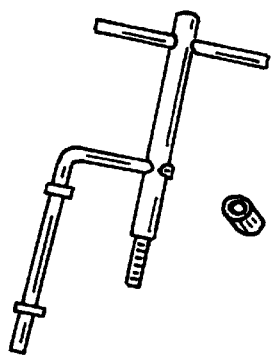
FIG. 10 is a photograph of an L-shaped rod with pins for attachment to a block-mounted arm, a pinion for activating a block, and a wrench for the pinion.
Figure 9:
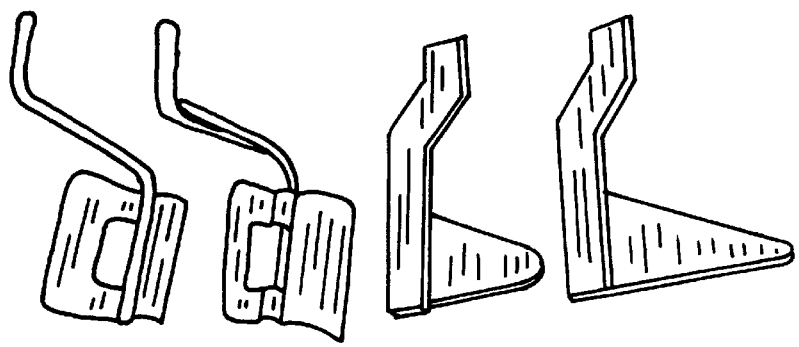
FIG. 9 is a photograph showing various grips usable with the invention.
Figure 11:
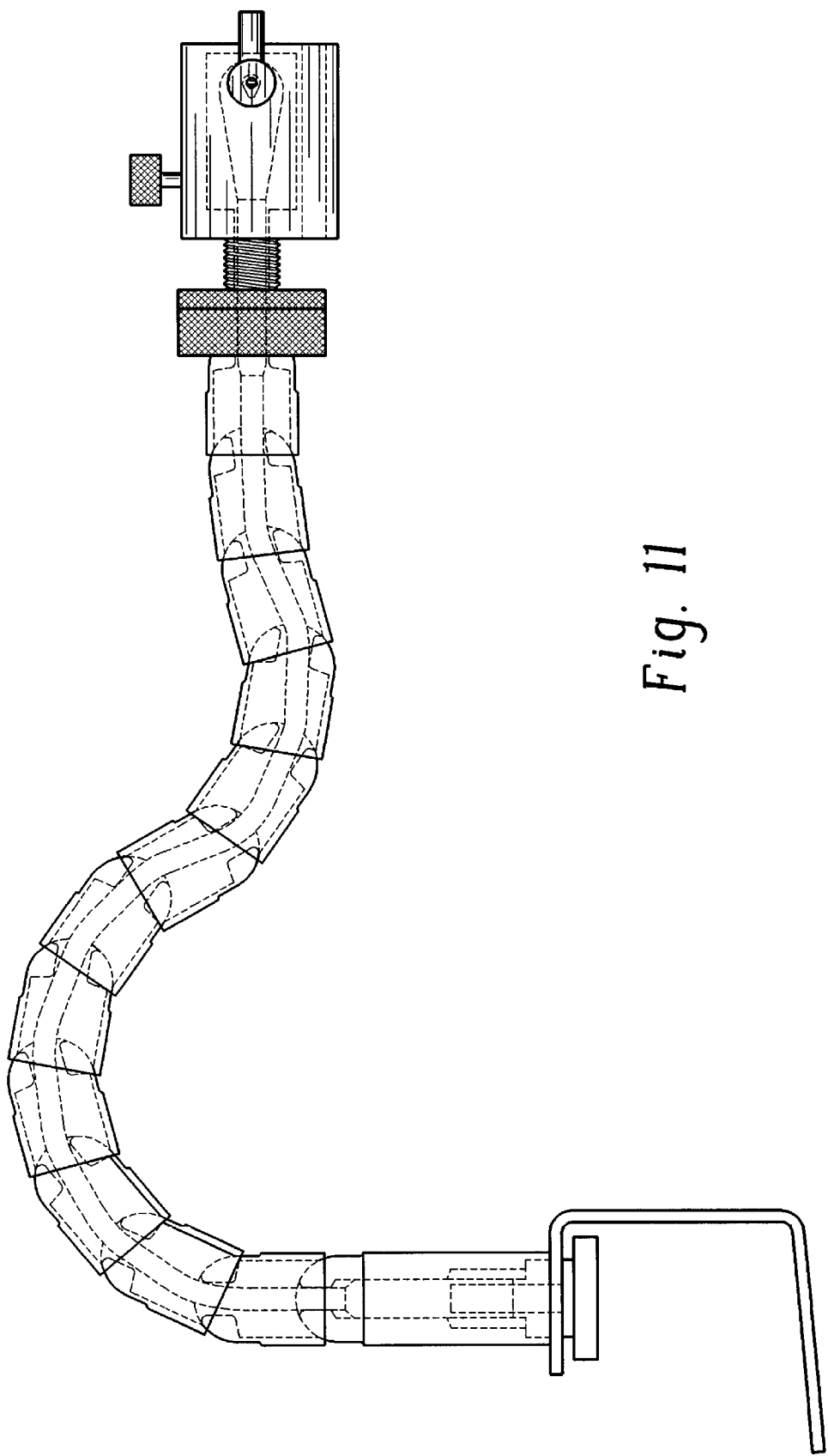
FIG. 11 is a side elevational view of a retractor in the form of a stabilizer and a flexible holder therefor in accordance with the invention.
Figure 12:
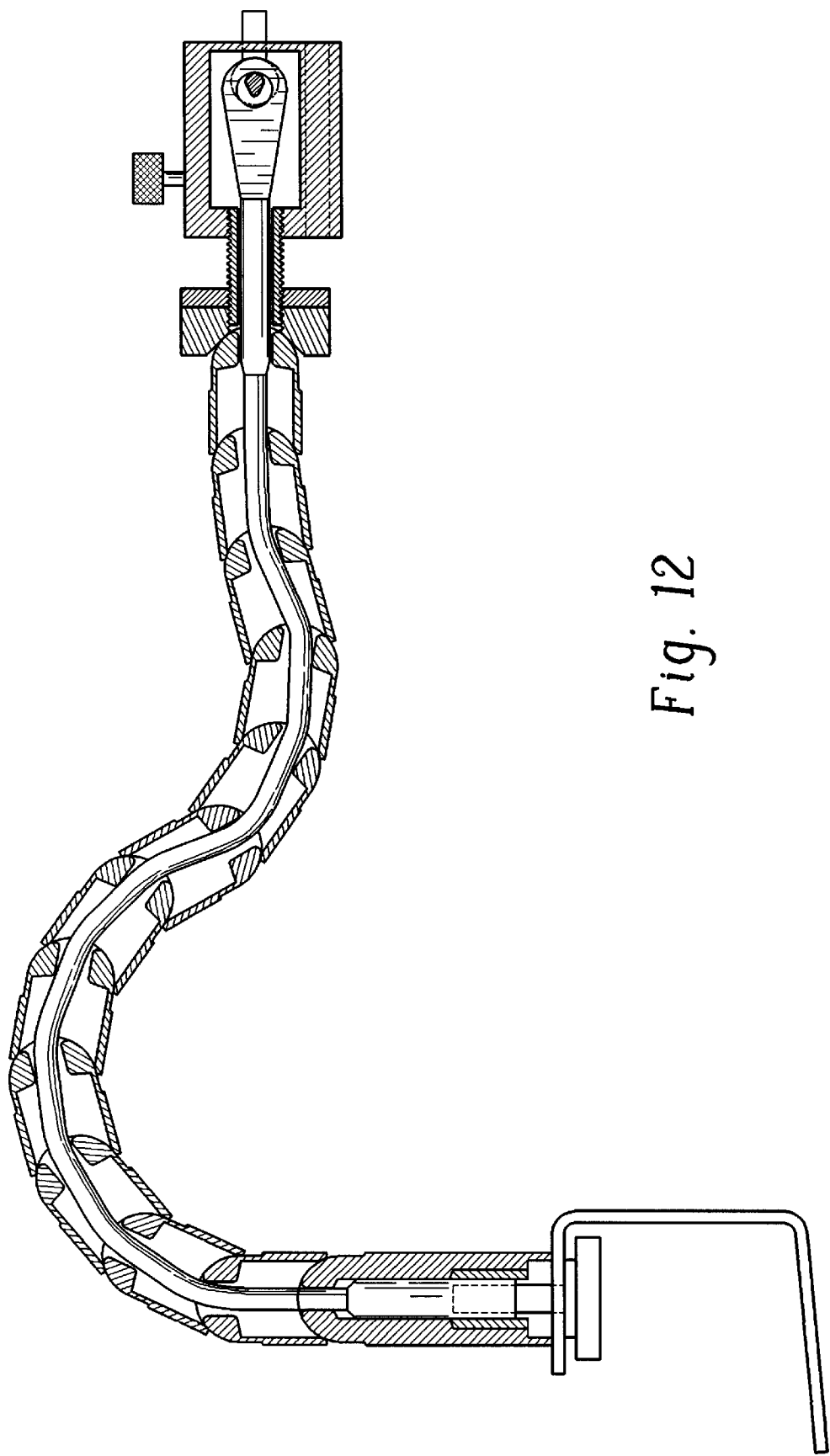
FIG. 12 is a cross-sectional view of the holder of FIG. 11.
Figure 13:
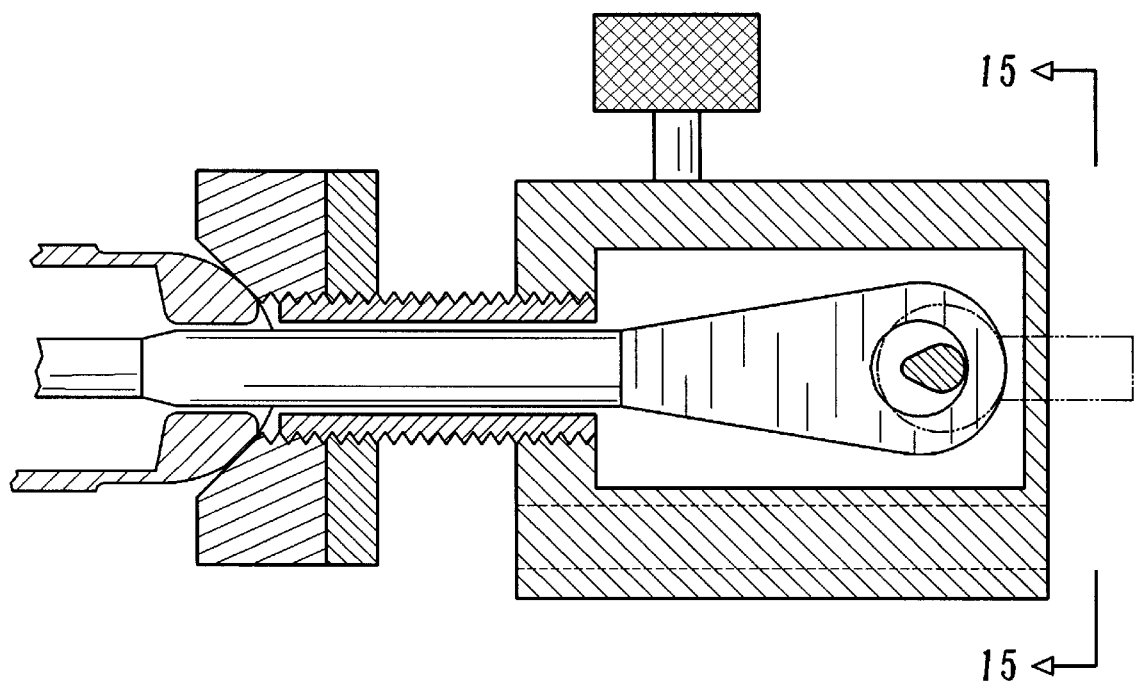
FIGS. 13 and 14 are cross-sectional views of a portion of the holder of FIG. 11 showing a cable-tightening cam in tightened and loosened positions.
Figure 14:
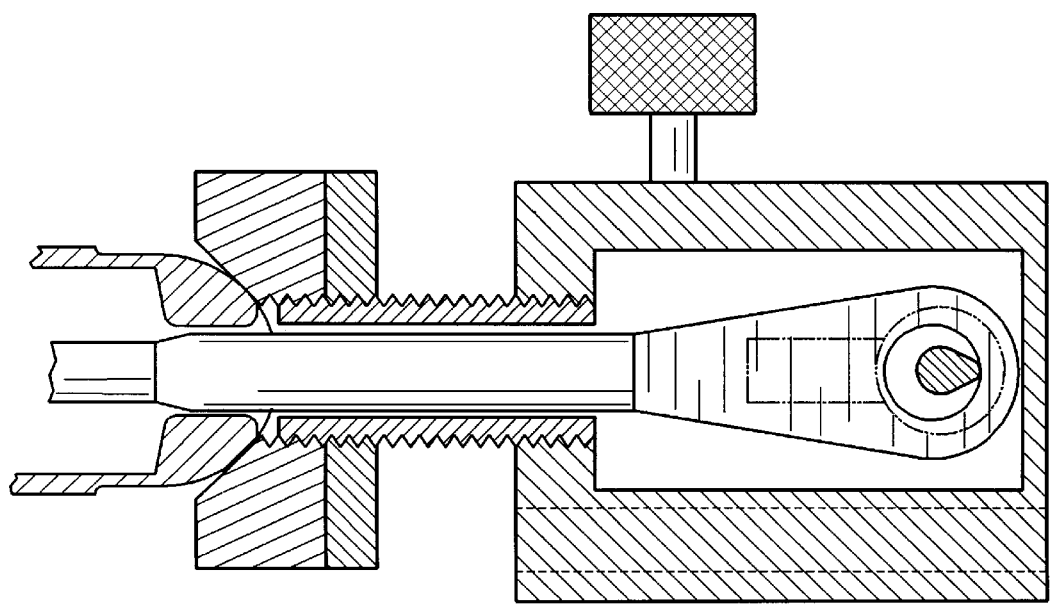

The various stabilizer versions described heretofore include a handle that can be connected to the rod shown in FIGS. 7 and 10 by means of a universal clamp. Yet another version of the stabilizer is shown in FIGS. 6 and 11–17 that is connected to the retractor 10 by a different technique. In this version of the stabilizer, a selectively flexible connection between the neck and a selected block 32, 34 is established. The connection includes a housing from which a threaded fitting extends. A nut and a locknut are threaded onto the fitting. A plurality of generally tubular members are disposed in end-to-end relationship. The neck of the stabilizer is connected to a fitting at the end of the tubular members by means of a threaded pin. A cable is connected to the fitting and is threaded through the tubular members, through the fitting, and into the housing. The end of the cable includes a formation having an opening therein. A cam (eccentric) is disposed within the opening (FIGS. 13 and 14). A handle is connected to the cam and is disposed outside the housing.

Figure 15:
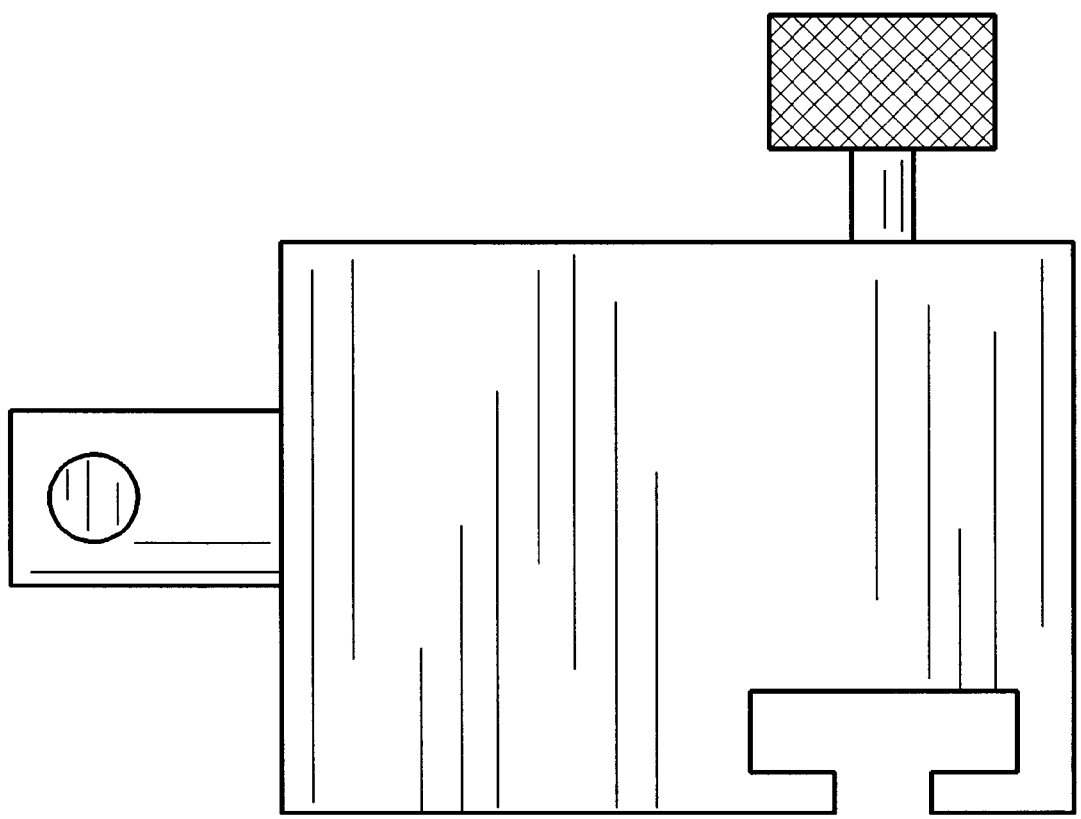
FIG. 15 is an end view of the holder of FIG. 11 taken along a plane indicated by line 15—15.
Figure 16:
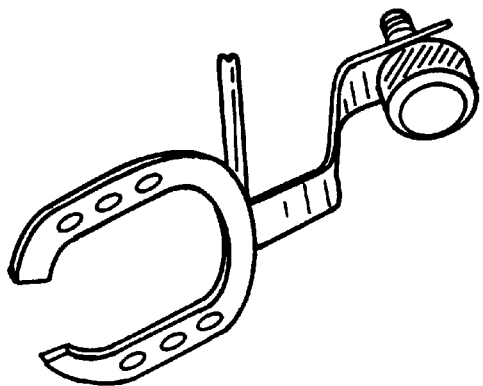
FIG. 16 is a perspective view of another embodiment of a stabilizer having a suction capability.

Referring to FIG. 15, the housing includes a longitudinally extending "T-slot" that opens through the lower face of the housing. The T-slot can be fitted over one of the bars 47 and secured there by tightening a set screw that opens into the upper portion of the T-slot. As will be apparent from an examination of FIGS. 11–15, the tension on the cable, and hence the compression force applied to the tubular members, can be pre-set by adjusting the nut and the locknut that are threaded onto the fitting projecting from the housing. Thereafter, the tension on the cable can be increased even more by rotating the handle to move the cam and the formation.

Figure 17:
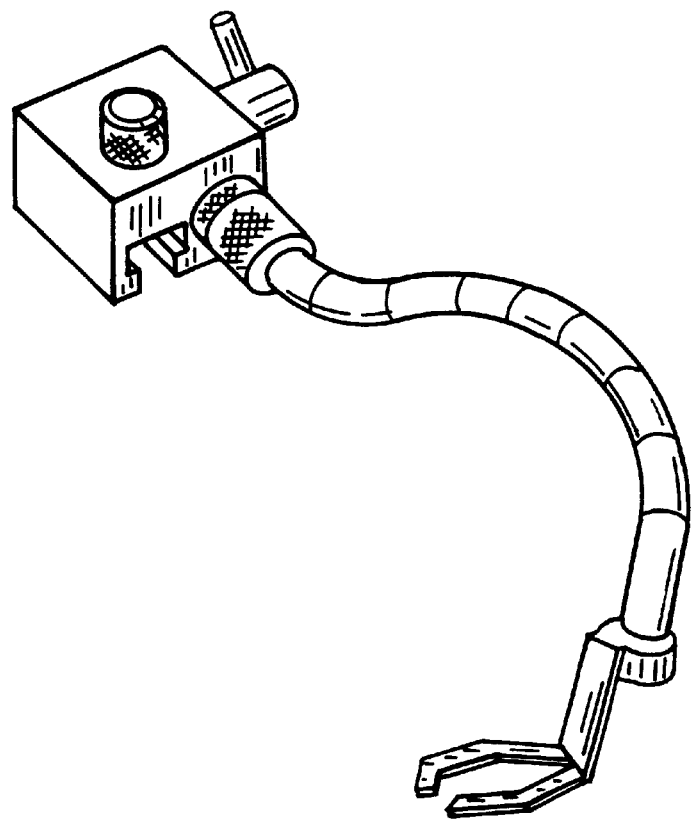
FIG. 17 is a perspective view of the stabilizer of FIG. 11.
Figure 18:
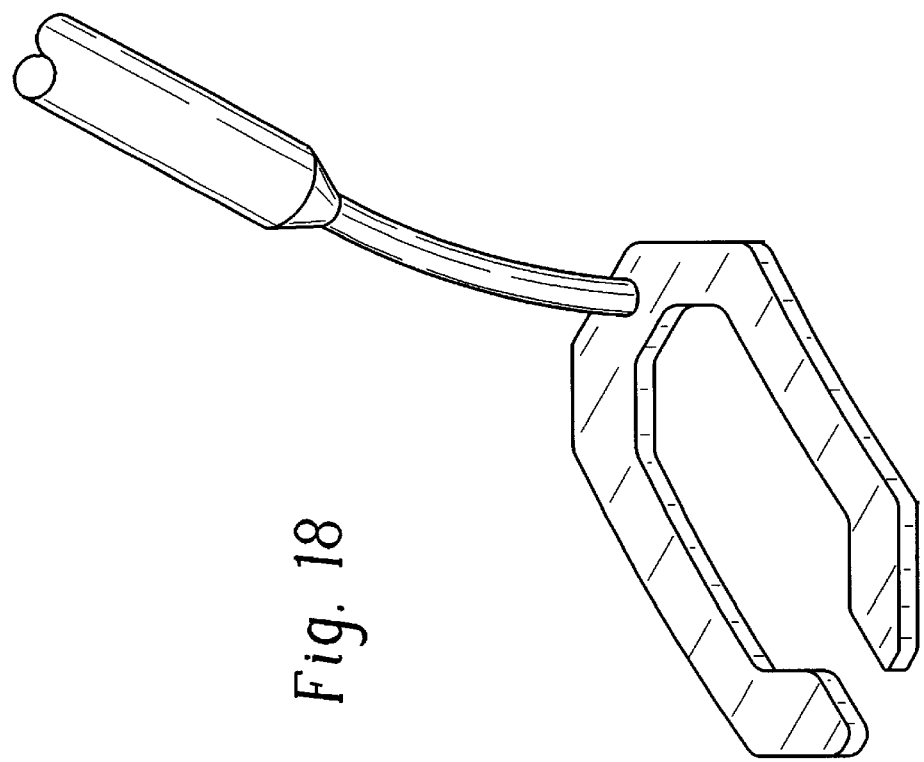
FIGS. 18, 19, and 20 are perspective, side, and bottom views, respectively, of a stabilizer according to the invention having a malleable neck.

Referring particularly to FIG. 17, the fingers can be made hollow with openings on the underside. A hollow tube (or handle) is connected to the fingers. A vacuum can be applied to the fingers through the tube (or handle) in order to withdraw blood or other fluids through the openings in the fingers.

Referring to FIG. 10, an extra pinion is shown. The pinion includes a drive opening in the form of a hexagonal socket. The invention also includes a wrench having a hexagonal end for establishing a driving connection with the pinion. If desired, the handles and pinions shown in FIG. 8 can be removed from the blocks 32, 34 upon advancing the blocks 32, 34 beyond the ends of the crossbar 16 (to disengage the teeth). At that point, the pinions, with handles attached, can be removed from the blocks 32, 34. Then, the pinions shown in FIG. 10 can be inserted into the blocks 32, 34. The wrench then can be used to move the blocks 32, 34 back and forth on the crossbar 16. The use of this unobtrusive pinion is preferred in situations where space is at a premium or the handles otherwise might be considered to be obstructive.

Figure 5:
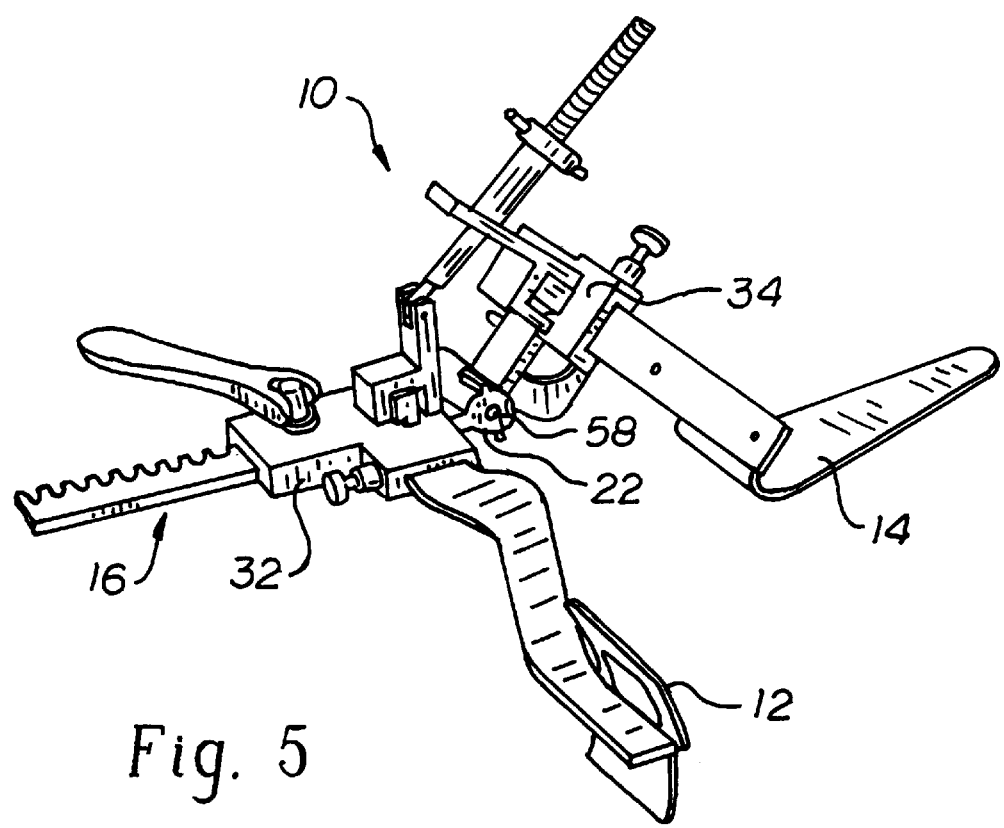
FIG. 5 is a perspective view of the retractor of FIG. 1 with a threaded-rod pivoting device and different grips.
Figure 6:
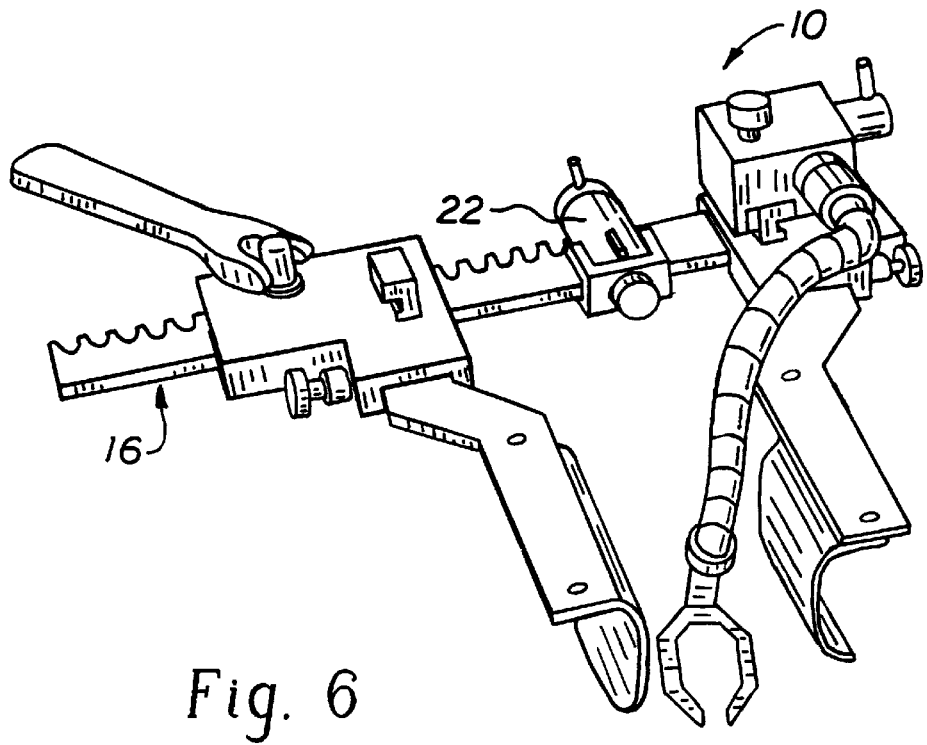
FIG. 6 is a perspective view of the retractor of FIG. 1 without a pivoting device and with a stabilizer held in place by a selectively flexible holder.

Referring now to FIG. 5, another form of pivoting device is shown. The device includes a first bracket extending vertically upwardly from the block 32 to which an elongate, threaded rod is pivotally connected at the upper end thereof. A second bracket is connected to the block 34 and extends vertically upwardly therefrom. The second bracket includes an opening through which the rod extends. A nut is threaded onto the rod. The opening is rounded on that side engaged by the nut. The nut also is rounded on that end which engages the bracket.

As will be apparent from an examination of FIG. 5, tightening or loosening of the nut will cause the brackets to be moved closer to each other or further apart. In turn, the grips 12, 14 will be pivoted relative to each other. That portion of the rod that extend between the brackets is largely unthreaded. Accordingly, the rod can receive retractor blade-supporting clamps at a location between the brackets. This feature provides an extra degree of versatility for the surgeon.

The method according to the invention comprises a particular technique for retracting the patient's ribs or sternum most effectively. The method in question involves compressing the distal ribs (usually the fourth and fifth ribs), while retracting and raising the adjacent proximal ribs (usually the second and third ribs). This result is accomplished by orienting the crossbar such that the movable grip is on the distal side of the patient.

Initially, the hinge is positioned to provide a straight crossbar and the grips are moved together in order to insert them between the ribs. The means for pivoting is actuated in order to pivot the fixed, or proximal, grip about the axis of the hinge. Then, the grips are moved apart by moving the distal grip along the crossbar. As the distal grip is moved, the grips are spaced further apart and the proximal grip is raised even further. Such retraction provides adequate access to the heart despite the small incision between the ribs.

The retractor according to the invention can be used for operations on either side of the chest. By orienting the crossbar appropriately, the retractor can always be positioned to compress the distal ribs and retract and raise the proximal ribs. A similar result can be obtained with incisions through the sternum, that is, appropriate positioning of the blocks and brackets will enable either side of the sternum to be retracted and raised as may be desired.

As will be appreciated from the foregoing description, the retractor according to the invention is minimally invasive. By using the retractor according to the invention, there is no need to perform a full sternotomy in order to have access to the heart. The foregoing results are obtained by using very small grips and using the retractor first as a rib-spreader and then as a proximal rib-lifter. Once the ribs have been retracted and raised properly, various attachments can be connected to the retractor for purposes of cardiovascular retraction and other purposes.

The retractor according to the invention also can be used for other types of surgeries, such as spinal implant surgery. The retractor can be used for both anterior and posterior spinal implant surgery. The ability to pivot the grips relative to each other is a significant advantage compared with existing retractors. Further, because the grip-carrying arms are removably connected to the retractor, it is possible to substitute different grips to conduct different types of surgical procedures. Such substitutions can be accomplished quickly and easily, thereby enhancing the versatility of the retractor.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A surgical retractor, comprising:
    an elongate crossbar having a first portion that defines a longitudinal axis, a second portion that defines a longitudinal axis, and a hinge connecting the first and second portions;
    a first grip connected to the first portion and movable therealong;
    a second grip connected to the second portion;
    a first movement device for moving the first grip along the first portion toward or away from the second grip; and
    a pivoting device for pivoting the first and second portions relative to each other about an axis perpendicular to the longitudinal axes of the first and second portions.

2. The retractor of claim 1, further comprising a tightening means for selectively tightening the hinge in a desired position.

3. The retractor of claim 2, wherein the tightening means comprises a threaded pin that connects the first and second portions, the pin having an enlarged nut that enables the user to tighten or loosen the pin by hand.

4. The retractor of claim 1, further comprising a lock for securing the first and second portions in a position where the longitudinal axes lie in a common plane.

5. The retractor of claim 4, wherein the lock comprises a plurality of spaced prongs, the prongs engaging opposite sides of the first and second portions.

6. The retractor of claim 5, wherein the prongs are connected to and extend from a base plate, the lock further comprising:
    an opening in the base plate;
    a threaded opening in the hinge; and
    a threaded pin carried by the base plate and extending through the opening, the pin engagable with the opening in the hinge to secure the lock to the hinge.

7. The retractor of claim 1, wherein a plurality of teeth are disposed along one edge of the first portion of the crossbar, and wherein the first movement device comprises a pinion engagable with the teeth and a handle connected to the pinion.

8. The retractor of claim 1, wherein the second grip is fixedly connected to the second portion.

9. The retractor of claim 1, wherein the second grip is movable along the second portion, and further comprising a second movement device for causing the second grip to be moved along the second portion toward or away from the first grip.

10. The retractor of claim 9, wherein a plurality of teeth are disposed along one edge of the second portion of the crossbar, and wherein the second movement device comprises a pinion engagable with the teeth and a handle connected to the pinion.

11. The retractor of claim 9, wherein a plurality of teeth are disposed along one edge of the second portion of the crossbar, and wherein the second movement device comprises:
    a pinion engagable with the teeth, the pinion having a drive portion; and
    a wrench engagable with the drive portion.

12. The retractor of claim 1, further comprising:
    first and second blocks mounted on the first and second portions, respectively, and;
    first and second arms, each having one end to which the first and second grips are connected, respectively, the first and second arms being connected at their other ends to the first and second blocks, respectively.

13. The retractor of claim 12, wherein the arms are removably connected to the blocks, the removable connection being established by:
    a notch formed in the arms at that portion of the arms connected to the blocks; and
    a spring-biased pin carried by each of the blocks, the pins being engagable with the notches.

14. The retractor of claim 12, further comprising a rod connected to a selected one of the arms, the rod being generally parallel with the arm and spaced a predetermined distance thereabove.

15. The retractor of claim 14, wherein the rod is removably connected to the arm, the removable connection being established by a pair of spaced openings in the upper surface of the arm and a pair of pins projecting from the lower surface of the rod, the pins being of a size and shape to fit into the openings.

16. The retractor of claim 14, further comprising:
    a retractor blade having a handle; and
    a clamp connected to the rod, the clamp having an opening through which the handle extends.

17. The retractor of claim 16, wherein the clamp includes a first portion engagable with the rod, a second portion engagable with the handle, and a threaded pin connecting the first and second portions, the pin, upon tightening, causing the first and second portions to be moved toward each other so as to securely engage the rod and the handle, respectively, and prevent relative movement therebetween.

18. The retractor of claim 16, wherein the retractor blade is in the form of a stabilizer having a pair of spaced, generally flat fingers that are connected to the handle, the fingers lying in a plane disposed at an angle from the longitudinal axis of the handle.

19. The retractor of claim 18, wherein the fingers are made of a malleable material.

20. The retractor of claim 18, further comprising a malleable neck disposed intermediate the fingers and the handle.

21. The retractor of claim 18, further comprising serrations on the underside of the fingers.

22. The retractor of claim 18, wherein the fingers are hollow, and further comprising openings on the underside of the fingers.

23. The retractor of claim 18, further comprising:
a neck portion that connects the fingers to the handle;
a ball rigidly secured to the end of the neck;
a socket at the end of the handle into which the ball can be nested; and
a sleeve threaded to the end of the handle about the ball, the sleeve, upon being tightened, compressing the ball into the socket.

24. The retractor of claim 12, further comprising:
a housing secured to the upper surface of a selected block;
a stabilizer having a pair of spaced, generally flat fingers, the stabilizer being connected to the housing; and
the connection between the stabilizer and the housing being established by a flexible member that can be secured in a rigid position when desired.

25. The retractor of claim 24, wherein the housing includes a slot in that portion of the housing in contact with the block, and the block includes a mounting bar secured thereto, the slot and mounting bar being configured to engage each other in a secure, sliding relationship.

26. The retractor of claim 24, wherein the flexible member includes:
a plurality of generally tubular members disposed in end-to-end relationship;
a cam disposed within the housing;
a fitting disposed at the end of the generally tubular members;
a cable extending through the generally tubular members, the cable being connected at one end to the cam and being connected at the other end to the fitting, activation of the cam causing the cable to be tightened or loosened.

27. The retractor of claim 26, further comprising;
a threaded member projecting from the housing, the cable extending through the threaded member; and
a nut carried by the threaded member, the nut being in engagement with the generally tubular member closest to the housing such that movement of the nut back and forth on the threaded member causes the generally tubular members to be tightened or loosened.

28. The retractor of claim 1, wherein the pivoting device includes a first vertically extending bracket connected to the first portion, a second vertically extending bracket connected to the second portion, and a connector extending between the first and second brackets, the connector being adjustable to permit the first and second brackets to be spaced apart a desired distance.

29. The retractor of claim 28, wherein the connector includes:
an elongate cylindrical rod having first and second ends, the first end being pivotally connected to the first bracket and the second end being threaded;
an opening in the second bracket through which the second end of the cylindrical rod extends; and
a nut disposed on the second end of the cylindrical rod.

30. The retractor of claim 28, wherein the connector is a toothed rod affixed to the first bracket, and the second bracket includes an opening through which the toothed rod extends, and further comprising:
a pinion included as part of the second bracket in engagement with the teeth; and
a spring-biased pawl carried by the second bracket, the pawl permitting the brackets to be moved toward each other while preventing the brackets from being moved away from each other.

31. The retractor of claim 28, wherein the first and second brackets are removably connected to the first and second portions.

32. The retractor of claim 31, wherein each of the first and second brackets includes a slot in that portion of the bracket in contact with the block, and each block includes a mounting bar secured thereto, the slots and mounting bars being configured to engage each other in a secure, sliding relationship.

33. The retractor of claim 31, wherein each of the first and second brackets includes a generally U-shaped member extending from the lower side thereof, and each block includes a mounting bar that defines an undercut portion, the U-shaped members being of a size and shape to be fitted into the undercut portion.

34. A method of surgical retraction, comprising the steps of:
providing a surgical retractor having an elongate crossbar with a first portion that defines a longitudinal axis, a second portion that defines a longitudinal axis, and a hinge connecting the first and second portions, a first grip connected to the first portion and moveable therealong, a movement device for moving the first grip along the first portion toward or away from the second grip, and a pivoting device for pivoting the second portion relative to the first portion about an axis perpendicular to the longitudinal axes of the first and second portions, and a second grip connected to the second portion;
moving the first grip along the first portion until it is adjacent to the second grip;
inserting the first and second grips into an incision in a patient's body;
actuating the pivoting device to pivot the first and second grips relative to each other; and
moving the first grip away from the second grip to expand the opening in the patient's body.

35. The method of claim 34, comprising the additional steps of:
providing an elongate rod as part of the pivoting device;
providing a retractor blade having a portion adapted to engage a second portion of the patient's body, the retractor blade having a longitudinally extending handle;
connecting the retractor blade to the rod;
engaging the retractor blade with the second portion of the patient's body; and
locking the retractor blade in a fixed position relative to the rod.

36. The method of claim 35, comprising the further steps of disposing the rod in spaced relationship to the crossbar and aligning the rod generally parallel with the crossbar.

37. The method of claim 35, wherein the portion of the retractor blade that engages the second portion of the patient's body includes a pair of spaced, generally flat fingers that are connected to the handle, the fingers lying in a plane disposed at an angle of approximately 125 degrees from the longitudinal axis of the handle.

38. The method of claim 34, comprising the additional steps of:
providing an elongate rod;
connecting the elongate rod to a selected one of the grips, the elongate rod being positioned so that it is spaced a predetermined distance above the grip and extends along an axis parallel to the axis about which the second portion of the crossbar is pivoted relative to the first portion of the crossbar;

providing a retractor blade having a portion adapted to engage a second portion of the patient's body, the retractor blade having a longitudinally extending handle;

connecting the retractor blade to the elongate rod;

engaging the retractor blade with the second portion of the patient's body; and locking the retractor blade in a fixed position relative to the second rod.

39. The method of claim 38, wherein the portion of the retractor blade that engages the second portion of the patient's body includes a pair of spaced, generally flat fingers that are connected to the handle, the fingers lying in a plane disposed at an angle of approximately 125 degrees from the longitudinal axis of the handle.

* * * * *